United States Patent
Liu et al.

(10) Patent No.: US 9,423,373 B2
(45) Date of Patent: Aug. 23, 2016

(54) METHOD FOR DETECTING BIOCHEMICAL OXYGEN DEMAND

(75) Inventors: Changyu Liu, Changcbun (CN); Shaojun Dong, Changchun (CN)

(73) Assignee: Changchun Institute of Applied Chemistry, Chinese Academy of Science, Changchun, Jilin (CN)

( * ) Notice: Subject to any disclaimer, the term of this patent is extended or adjusted under 35 U.S.C. 154(b) by 216 days.

(21) Appl. No.: 14/359,037

(22) PCT Filed: Apr. 10, 2012

(86) PCT No.: PCT/CN2012/073691
§ 371 (c)(1),
(2), (4) Date: May 16, 2014

(87) PCT Pub. No.: WO2013/152474
PCT Pub. Date: Oct. 17, 2013

(65) Prior Publication Data
US 2014/0326617 A1    Nov. 6, 2014

(51) Int. Cl.
*G01N 27/26* (2006.01)
*G01N 33/18* (2006.01)
*G01N 15/00* (2006.01)

(52) U.S. Cl.
CPC .......... *G01N 27/26* (2013.01); *G01N 33/1806* (2013.01); *G01N 33/1866* (2013.01); *G01N 2015/0088* (2013.01)

(58) Field of Classification Search
CPC .. G01N 27/327; G01N 27/30; G01N 27/416; G01N 35/00; G01N 33/1806; G01N 33/1866; G01N 2015/0088
See application file for complete search history.

(56) References Cited

U.S. PATENT DOCUMENTS

| 5,356,792 A | 10/1994 | Maeda et al. |
| 2008/0006539 A1 | 1/2008 | Kumar et al. |

FOREIGN PATENT DOCUMENTS

| CN | 101413915 A | 4/2009 |
| CN | 101413915 A * | 4/2009 |
| CN | 101639472 A | 2/2010 |

OTHER PUBLICATIONS

Machine translation Dec. 21, 2015 CN 101413915 A.*

(Continued)

*Primary Examiner* — Jennifer Dieterle
(74) *Attorney, Agent, or Firm* — Lewis Roca Rothgerber Christie LLP

(57) ABSTRACT

The present invention provides a method for detecting biochemical oxygen demand. Active sludge, surface water, domestic waste water, or industrial waste water comprising microorganism is taken as a water sample with microorganism in the method provided by the present invention. The water sample with microorganism is cultivated to obtain a microorganism film. The blank water sample and the target water sample are made to pass through the microorganism film respectively. The dissolved oxygen reduction current values of the blank water sample and the target water sample are detected. The difference value between the dissolved oxygen reduction current value of the target water sample and that of the blank water sample is obtained. On the basis of the difference value and the predetermined standard curve, the biochemical oxygen demand of the target water sample is acquired. The method provided by the present invention adopts active sludge, surface water, domestic waste water, or industrial waste water comprising microorganism as the water sample with microorganism. The environmental adaptability of the prepared microorganism film is strong, so that one or more of tap water, well water, atmospheric water, or ground water may serve as medium to maintain the physiological activity with no need of providing a buffer solution system.

12 Claims, 3 Drawing Sheets

(56) References Cited

OTHER PUBLICATIONS

International Search Report of corresponding PCT/CN2012/073691, dated Jan. 17, 2013, 6 pages.

Chee, et al., "Biosensor for the estimation of low biochemical oxygen demand," Analytica Chimica Acta, vol. 379, No. 1-2, Jan. 11, 1999, pp. 185-191.

* cited by examiner

METHOD FOR DETECTING BIOCHEMICAL OXYGEN DEMAND

CROSS-REFERENCE TO RELATED APPLICATION(S)

This application is a National Phase Patent Application and claims priority to and the benefit of International Application Number PCT/CN2012/073691, filed on Apr. 10, 2012, the entire disclosure of which is incorporated herein by reference.

FIELD OF THE INVENTION

The present invention relates to the technical field of environmental protection, and in particular to a method for testing biochemical oxygen demand (BOD).

BACKGROUND

BOD refers to the amounts of dissolved oxygen (DO) consumption when some substances especially organic substances in water that can be biologically decomposed by microorganisms. For example, the BOD is called five-day BOD ($BOD_5$) if biological oxidation is performed for five days. BOD is an important index for analyzing the content of organic pollutants in water, and is one of the most important parameters for conventional monitoring of water quality, whose higher values mean more organic pollutants in the water and more serious pollution.

At present, the method of diluting and inoculating is commonly adopted internationally for testing the BOD, which is also called $BOD_5$ method. However this method has the disadvantages of time consuming, intensive work load, complex operations, various interference factors, and poor repeatability. Also, it can not reflect the change of water quality timely, and does not allow the on-line testing of water quality.

For the purpose of overcoming the above disadvantages, a variety of methods for testing BOD have been developed in the prior art. One example is microbial sensor method, which comprises the steps of cultivating the target microorganisms, centrifuging the cultured microorganisms, quantifying and physically adsorbing the microorganisms on the surface of a cellulose membrane or dialysis membrane and the like to provide a biological membrane (biofilm), or chemically embedding the microorganisms by using sol-gel polymers to provide a biofilm; and closely attaching the obtained biofilm to the surface of an oxygen electrode, when a target water sample flows through the surface of the biofilm, microbial respiration is enhanced, oxygen consumption increases, therefore the oxygen content tested by the oxygen electrode is reduced. In the method, BOD of a water sample is obtained by use of the principle that microbial respiration is proportional to the content of organic matters. One example is a mediator method, which adopts an artificial electron acceptor, such as potassium ferricyanide to substitute natural electron acceptor oxygen, and thus improves the degradation efficiency of organic matters by microorganisms, and improves the accuracy of the testing results. One example is a biofilm reactor method, which utilizes the enriched microbial population to degrade organic matters, and achieves the measurement on the BOD in water by testing the change of DO content. In order to maintain a stable microbial population, this biofilm reactor method needs continuous supplementation of organic matters, so that the operation is complex and the maintenance cost is high. In prior art, a microbial fuel cell method is also used for testing BOD, which mainly depends on the generation of a current when the enriched microbial population degrade organic matters, and determines the value of BOD in water according to the intensity of the current.

The above methods for testing the BOD in water are all based on the action of microorganisms on organic matters, including microbial respiration and the degradation of the organic matters by the microorganisms. In order to maintain the physiological activity of the microorganisms, a certain level of pH value and osmotic pressure are provided therefore. In the prior art, a buffer solution system is provided for the survival of the microorganisms, and the most commonly used ones of which include phosphate buffer solution and Tris-HCl buffer system. However, the phosphate buffer solution will result in secondary pollution on the environment and Tris-HCl buffer system is expensive and not suitable for on-line monitoring. In the prior art, there is no method for testing the BOD in water that does not adopt a buffer system.

SUMMARY OF THE INVENTION

The object of the present invention is to provide a method for testing BOD, which allows the testing of BOD in water without using a buffer system.

The present invention provides a method for testing (detecting) BOD, comprising the steps of:
  a) subjecting an air-saturated microorganism-containing water sample to microorganism cultivation to obtain a biofilm;
  b) allowing an air-saturated blank water sample to pass through the biofilm obtained in said step a), and testing and determining a DO reduction current of said blank water sample;
  c) allowing an air-saturated target water sample to pass through the biofilm which has been subjected to said step b), and testing and determining a DO reduction current of said target water sample;
  d) calculating the difference between the DO reduction current of said blank water sample and the DO reduction current of said target water sample according to the DO reduction current of the blank water sample obtained in said step b) and the DO reduction current of the target water sample obtained in said step c); and
  e) determining BOD of the target water sample according to the difference obtained in said step d) and a predetermined standard curve;
said microorganism-containing water sample is activated sludge, surface water, domestic sewage or microorganism-containing industrial wastewater;
and said blank water sample is one or more selected form tap water, well water, rain water and groundwater.

Preferably, said microorganism-containing water sample (microorganism source) is activated sludge, surface water or microorganism-containing industrial wastewater.

Preferably, said step a) specifically comprises:
  a1) at 20□-45□, subjecting an air-saturated microorganism-containing water sample to microorganism primary cultivation to obtain a primary biofilm;
  a2) allowing an air-saturated blank water sample to pass through the primary biofilm obtained in step a1) to purge the primary biofilm, until a stable DO reduction current is obtained;

a3) allowing an air-saturated standard solution to pass through the primary biofilm purged in said step a2), and testing and determining DO reduction current of said standard solution;

a4) repeating the step a1) to step a3), until the tested DO reduction current of the standard solution is stable, so as to complete the microorganism cultivation and obtain a biofilm.

Preferably, the blank water sample in said step b) is one or two of tap water and groundwater.

Preferably, the time for microorganism cultivation in said step a) is 20-300 h.

Preferably, the standard curve in said step e) is obtained according to the steps of:

preparing air-saturated standard solutions with series BOD concentrations by use of said blank water sample as solvent;

allowing an air-saturated blank water sample to pass through the biofilm obtained in said step a), and testing and determining a stable DO reduction current of said blank water sample;

allowing said standard solutions to pass through the biofilm through which said blank water sample having passed through, and testing and obtaining the DO reduction currents of said standard solutions;

determining the differences between the DO reduction current of said blank water sample and the DO reduction currents of said standard solutions according to the DO reduction current of said blank water sample and the DO reduction currents of said standard solutions;

and determining a standard curve according to said differences and the BOD concentrations of said standard solutions.

Preferably, said standard solution is a glucose solution, a glutamic acid solution, a glucose glutamic acid (GGA) mixed solution or a sucrose solution.

Preferably, the BOD concentration of said standard solution is 1.0 mg $O_2$/L-60.0 mg $O_2$/L.

Preferably, the microorganism cultivation in said step a) is carried out in a reactor.

Preferably, said reactor is tubular;

the material of said reactor is glass, ethylene-vinyl acetate copolymer, plastic, nylon, quartz or silicone;

the length of said reactor is 30.0 cm-420.0 cm;

and the inner diameter of said reactor is 1.0 mm-4.0 mm.

The present invention provides a method for testing BOD. In the method, an air-saturated microorganism-containing water sample is subjected to microorganism cultivation to obtain a biofilm, and said microorganism-containing water sample is selected from activated sludge, surface water, domestic sewage or microorganism-containing industrial wastewater; after an air-saturated blank water sample and a target water sample sequentially pass through said biofilm, DO reduction currents of said blank water sample and target water sample are tested, wherein microorganisms decompose the organic pollutants in the target water sample and consume the DO therein, so that the difference of DO reduction current between said blank water sample and target water sample is achieved; according to the predetermined standard curve and the difference of DO reduction current between said blank water sample and target water sample, the BOD of the target water sample is obtained; and said blank water sample is one or more of tap water, well water, rain water and groundwater.

In the method for testing BOD in the present invention, said microorganism-containing water sample is selected from activated sludge, surface water, domestic sewage or microorganism-containing industrial wastewater. Microorganisms in these microorganism-containing water samples have relatively strong inherent adaptive capacity to environment, and the biological activity thereof is not obviously affected by the change of pH value and ion concentration of the water system. Therefore the biofilm obtained by performing microorganism cultivation for the microorganisms also has relatively strong adaptive capacity to environment. Said tap water, well water, rain water or groundwater contain various kinds of microelements, a certain amount of metal ions and trace amount of organic matters. If the obtained biofilm is placed in a system of one or more of tap water, well water, rain water or groundwater, these conditions in the system are sufficient to make the biofilm maintain normal biological activity, so that the determination for the BOD of a target water sample can be realized without the need of providing a conventional buffer solution system.

Therefore, the testing method provided by the present invention reduces testing cost and labor cost, such as avoiding the consumption of a buffer reagent, the preparation of pure water and the preparation of a buffer solution. Furthermore, the testing method provided by the present invention avoids the secondary pollution caused by buffer solution such as phosphates. In addition, the present invention adopts one or more of tap water, well water, rain water or groundwater as a blank water sample, and the organic matter content therein is relatively low. The oxygen consumption by this organic matter is small and is regarded as that caused by endogenous respiration, which is deducted from the testing value for a blank water sample. Further, heavy metal ions in target water sample easily react with the anions in said blank water sample to form precipitates, which reduces the influence of the heavy metal ions on BOD testing. Due to the above facts, the testing result obtained in the present invention has higher accuracy.

In addition, the method for testing BOD of the present invention can complete the testing process for a target water sample in about 10 min, which improves the testing speed. The prepared biofilm in the present invention is less likely to peel off, and impurities are easier to remove, so that the blockage for the testing system can be avoided. Further, during the testing process for a target water sample, microorganisms in the target water sample can substitute the inactivated microorganisms in the biofilm, so as to realize the self-restoring of the biofilm, which is in favor of the replacement between old and new biofilms. The prepared biofilm has the advantages such as higher stability, longer service life, and simpler maintenance in non-testing time i.e. just placing it in one or more of tap water, well water, rain water or groundwater under a room temperature condition. Experimental result shows that, the biofilm reactor of the present invention can be used continuously for more than one year and a half. Furthermore, after the biofilm is stored for 2 weeks, its signal response to organic matters is only decreased by about 13%; and when the storage time exceeds 2 months, its oxygen reduction current response value for organic matters is recovered to about 80% of the initial value after it is activated overnight with organic matters and tap water alternately, and its signal response value for organic matters is almost the same as the initial value after it is re-cultivated by a microorganism-containing water sample.

At the same time, the biofilm in the testing method of the present invention has higher biodegradation rate. Experimental result shows that the biofilm can decompose about 20% of organic matters in a target water sample, which indicates that the DO reduction current value of a target water sample in the present invention is obtained depending on the decomposition of most of organic matters therein, so that the obtained result is more reliable. Further, the biofilm in the present invention can realize nonselective decomposition or degradation for different types of organic matters, which means that the obtained DO reduction current value is only related with BOD concentration of a sample and has no significant relation with the type of the organic matter. In addition, the biofilm in the present invention has good poisoning resistance. Experimental result shows that heavy metal ion such as $Cr^{6+}$, $Cu^{2+}$, $Zn^{2+}$, $Ni^{2+}$ or $Mn^{2+}$ at a mass concentration up to 30.0 mg/L has no influence on the biofilm.

Further, the present invention can complete the cultivation for a biofilm in a reactor, and the biofilm can be directly grown on the inner wall of the reactor. Compared with a method adopting physical or chemical method to embed microorganisms to prepare a biofilm in prior art, the inventive method can reduce the diffusion resistance of oxygen gas and organic matters on the surface of the biofilm to a greater extent, so that the organic matters in a target water sample can be degraded fully by microorganisms, thus further improving the accuracy of the testing result.

DETAILED DESCRIPTION OF THE INVENTION

Figure 1:
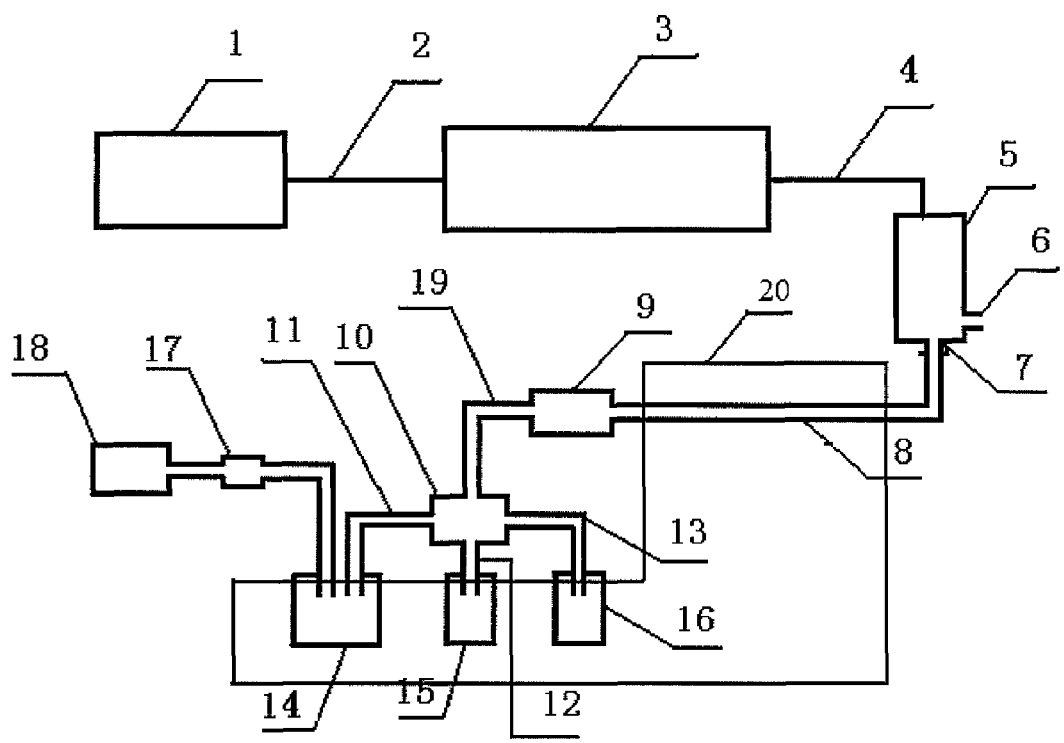
FIG. 1 is a flow chart of a BOD testing method provided by the present invention.

The present invention provides a method for testing BOD, comprising the steps of:
a) subjecting an air-saturated microorganism-containing water sample to microorganism cultivation to obtain a biofilm;
b) allowing an air-saturated blank water sample to pass through the biofilm obtained in said step a), and testing and obtaining the DO reduction current of said blank water sample;
c) allowing an air-saturated target water sample to pass through the biofilm obtained after performing said step b), and testing and obtaining the DO reduction current of said target water sample;
d) calculating the difference between the DO reduction current of said blank water sample and the DO reduction current of said target water sample according to the DO reduction current of the blank water sample obtained in said step b) and the DO reduction current of the target water sample obtained in said step c); and
e) determining the BOD of the target water sample according to the difference obtained in said step d) and a predetermined standard curve;

said microorganism-containing water sample is activated sludge, surface water, domestic sewage or microorganism-containing industrial wastewater;
and said blank water sample is one or more of tap water, well water, rain water or groundwater.

Preferably, said microorganism-containing water sample (microorganism source) is activated sludge, surface water or microorganism-containing industrial wastewater.

BOD (BOD) refers to the amount of DO consumed in biochemical processes carried out by microorganisms decomposing some substances that can be oxidized, especially organic matters, in water, under the prescribed conditions. The BOD is a comprehensive index for reflecting the content of organic pollutants in water, and indicates the total amount of DO in water consumed when organic matters in water are subjected to oxidative decomposition under microbial biochemical action to be mineralized or gasified. The higher of the value of BOD means more organic pollutants in the water and more serious pollution.

In the method for testing BOD of the present invention, a microorganism-containing water sample is firstly subjected to microorganism cultivation under a certain condition to obtain a biofilm. In the present invention, the microorganism-containing water sample is obtained from activated sludge, surface water, domestic sewage or microorganism-containing industrial wastewater, and preferably activated sludge, surface water or microorganism-containing industrial wastewater. The present invention adopts a microorganism-containing water sample as the microbial source, and subjects it to microorganism cultivation to obtain a biofilm, which can achieve some advantages. For instance, the method provided by the present invention adopts the water sample which has microorganisms under natural conditions, and the microorganisms serve as microbial strain in the microorganism cultivation process. Under the conditions that both organic matters and oxygen gas are enough, the microorganisms can normally grow and propagate to form a biofilm. In the present invention, the microorganism-containing water sample serves as microbial source of the microorganism cultivation, and the microorganisms can maintain normal biological activity in natural environment, so that they have the ability to adapt to the external environment, and are insensitive to the change of system pH value and ion concentration. Therefore, under the condition that the present invention does not provide a buffer solution, the normal biological activity can be maintained and the testing for BOD of a target water sample can be realized.

The present invention adopts a microorganism-containing water sample as the microbial source of microorganism cultivation, said microorganism-containing water sample is activated sludge, surface water, domestic sewage or microorganism-containing industrial wastewater. The obtained biofilm retains its inherent adaptive capacity to environment, and still can keep its normal biological activity. The reasons are in that: the biofilm obtained by cultivating the microorganism-containing water sample has inherent adaptive capacity to environment of the microorganisms in the water sample, its activity is not obviously influenced by system pH value and ion concentration, and it is able to adapt to the environments of tap water, well water, rain water or groundwater; furthermore, tap water, well water, rain water or groundwater contains various kinds of microelements, a certain amount of metal ions and trace amount of organic matters, and these conditions are sufficient to meet the normal physiological activity of the microorganisms in the biofilm prepared in the present invention. Therefore, the testing method provided by the present invention has no need of providing a buffer solution for the testing system, on one hand, the cost of testing are reduced. For example, the consumption of a buffer reagent, the preparation of pure water and the preparation of a buffer solution are avoided. On the other hand, secondary pollution caused by buffer solution such as phosphates is avoided. Furthermore, one or more of tap water, well water, rain water and groundwater serve as a blank water sample, it will not cause significant errors on the testing result, because the organic matter content in tap water, well water, rain water or groundwater is relatively low, and the oxygen consumption of the organic matter can be regarded as endogenous respiration, and thus has been deducted in the testing process for a blank water sample. Therefore, the BOD value of a target water sample obtained by the testing method of the present invention has higher accuracy. Furthermore, heavy metal ions in the target water sample can easily complex with the anions in said blank water sample to form precipitates, which reduces the influence of the heavy metal ions on BOD testing, so as to further improve the accuracy of the testing result.

The invention adopts activated sludge as microorganism-containing water sample. The activated sludge is floccule formed from various kinds of organisms such as bacteria, fungi, protozoa and metazoa and inorganic substance such as metal hydroxide, etc., and has good adsorption, flocculation, biological oxidation and biosynthesis performances. The complex microorganisms in the activated sludge and organic nutrients in wastewater form complex food chains. The present invention adopts activated sludge as microorganism-containing water sample, the biofilm formed in the cultivation process by complex microbial population therein retains the inherent adaptive capacity to environment. Thus the activity of the obtained biofilm is not significantly influenced by the change of pH value and ion concentration, and the obtained biofilm still can keep normal biological activity in the environment provided by one or more of tap water, well water, rain water or groundwater, so that the biological activity of microorganisms can be maintained without the need of providing a buffer system. Therefore, the testing method of the present invention, on one hand, reduces the testing cost, such as avoiding the consumption of a buffer reagent, the preparation of pure water and the preparation of a buffer solution, on the other hand, avoids the secondary pollution caused by buffer solution such as phosphates. In the present invention, said blank water sample is preferably one or more of tap water, well water, rain water and groundwater, and more preferably one or two of tap water and groundwater.

The present invention also can adopt surface water as microorganism-containing water sample. Surface water is present in the surface of the earth's crust, and therein contains a large amount of microorganisms. The present invention adopts surface water as microorganism-containing water sample, and carries out microorganism cultivation for it, to obtain a biofilm. Microorganisms in the obtained biofilm have stronger vitality and environmental adaptability, and can exhibit their normal physiological activity in one or more of tap water, well water, rain water or groundwater, so that their biological activity can be maintained without the need of adding a buffer solution therein.

The present invention also can adopt domestic sewage as the microorganism-containing water sample. Domestic sewage refers to wastewater generated in daily life of human being, including family drainage water such as domestic fecal sewage, bath water, and kitchen water, etc. and commercial, hospital and amusement place drainage, etc. Domestic sewage contains a large amount of organic matters, such as cellulose, starch, saccharide, fat and protein, etc., also contains microorganisms and parasitic ovum. The large amount of organic matters in the domestic sewage facilitates microbial growth, so that the domestic sewage contains a wide variety of and a large amount of microorganisms. The present invention adopts said domestic sewage as the microorganism-containing water sample for constructing a biofilm, and the microorganisms in the resulting biofilm have stronger adaptive capacity to environment. The usage of one or more of tap water, well water, rain water or groundwater can meet the demands of their biological activity, so that there is no need of providing a buffer solution for microorganisms, which avoids the pollution of the commonly used buffer solution such as phosphate buffer solution, and reduces the testing cost.

The present invention also can adopt the microorganism-containing industrial wastewater as the microorganism-containing water sample. Industrial wastewater includes production wastewater and production sewage which are generated in industrial production process, and contains industrial production materials, intermediate products, byproducts and pollutants generated in the production process, such as textile wastewater, wastewater in food processing process and the like. The present invention adopts microorganism-containing industrial wastewater as the microorganism-containing water sample, and microorganisms in the industrial wastewater have relatively strong adaptive capacity to environment. The microorganism-containing water sample is subjected to microorganism cultivation, and thus the obtained biofilm retains inherent relatively high vitality and relatively strong adaptive capacity to environment of the microorganisms, and is not obviously influenced by the change of pH value and ion concentration of the system. Thus, in the present invention the adoption of one or more of tap water, well water, rain water or surface water as the survival medium of the biofilm can meet the demands of their biological activity, thus eliminating the need of providing a buffer solution, which avoids the pollution caused by the buffer solution such as phosphate buffer solution, and reduces the testing cost and labor cost.

In order to maintain the biological activity of microorganisms, suitable environment temperature is provided for microorganisms. The testing method for BOD provided in the present invention is preferably carried out at 20□ to 45□. The present invention preferably adopts a thermostatic water bath manner to provide the suitable temperature condition for microorganism cultivation. At said 20□-45□ temperature condition, the present invention preferably performs air saturation process for the microorganism-containing water sample to obtain air-saturated microorganism-containing water sample. Said air-saturated microorganism-containing water sample continuously flows through the surface of a microorganism carrier, so that microorganisms in said microorganism-containing water sample are gradually adsorbed and grow on the surface of said carrier to form a biofilm. In the present invention, the temperature of said thermostatic water bath is 20□ to 45□, and preferably 30□ to 37□.

When the present invention performs the cultivation of a biofilm, preferably said microorganism-containing water sample is subjected to microorganism cultivation in a reactor, and a biofilm is formed on the inner wall of the reactor, so as to obtain a biofilm reactor. In the present invention, said microorganism-containing water sample continuously flows through the reactor, microorganisms in said microorganism-containing water sample are adsorbed on the inner wall of said reactor and grow to obtain a biofilm reactor. The present invention has no specific limitation on the shape, material and size etc. of said reactor, and the reactor that is well known to those skilled in the art can be adopted. In the present invention, the material of said reactor can be glass, silicone, plastic, nylon, quartz or ethylene-vinyl acetate copolymer, and preferably glass; said reactor can be tubular, or in the shape of a hollow prism, and preferably tubular; the length of said reactor in the present invention is preferably 30.0 cm to 420.0 cm, more preferably 50.0 cm to 300.0 cm, and most preferably 75.0 cm to 150.0 cm; and the inner diameter of said reactor is preferably 1.0 mm-4.0 mm.

In order to make the inner wall of the reactor be more suitable for the adsorption and growth of microorganisms and facilitate the construction of a biofilm, the present invention preferably performs chemical modification for the inner wall of said reactor to obtain a reactor with roughened inner wall. The present invention has no special limitation on said chemical modification method, and the technical solution for roughening treatment that is well known to the skilled in the field can be adopted. In the present invention, hydrofluoric acid can be adopted to etch said reactor to obtain a reactor having roughened inner wall; a strongly alkaline solution can also be adopted to etch the inner wall of said reactor to obtain a reactor having roughened inner wall; and the inner wall of said reactor can be modified with a specific group such as hydroxyl, carboxyl or nanostructures, etc. to obtain a reactor having roughened inner wall, and said nanostructure is preferably carbon nanotubes.

In the process for cultivating microorganisms, the time for performing microbial primary cultivation in the present invention varies in terms of the sources of the microorganism-containing water sample. The present invention can control the cultivation time of the biofilm according to the amount of microorganisms contained in the microorganism-containing water sample. If the amount of microorganisms in the adopted microorganism-containing water sample is less, a longer microorganism cultivation time is adopted, and if the amount of microorganisms in the adopted microorganism-containing water sample is more, the time for microorganism cultivation can be shortened, as long as a biofilm with saturated adsorption is obtained. In the present invention, the time for biofilm cultivating is preferably 20 to 300 hours, more preferably 30 to 250 hours, and most preferably 35 to 150 hours.

When the present invention performs biofilm cultivating, the microorganism-containing water sample flows through the inner surface of a microbial carrier to obtain a biofilm. When said microorganism-containing water sample flows through the inner surface of said carrier, said microbial carrier will adsorb a certain amount of microorganisms. When organic matter-containing target water sample or standard solution flows through the carrier with a certain amount of microorganisms adsorbed thereon, these microorganisms can degrade the organic matters in said target water sample or standard solution, which results in the decrease of DO content of the target water sample or standard solution, which has been subjected to primary biofilm degradation and outflows from the terminal of said microbial carrier. But the stability of the biofilm obtained through the primary biofilm cultivation is relatively poor, because when the organic matters in said target water sample or standard solution are degraded by the biofilm, the biofilm still can grow on the inner wall of the primary biofilm reactor, which results in the continuous increase of the dimensions of biofilm in the process. In order to make the obtained biofilm have adsorption-saturated microorganisms, the present invention preferably performs the cultivation of a biofilm according to the steps of:

a1) at 20° C.-45° C., subjecting an air-saturated microorganism-containing water sample to microorganism primary cultivation to obtain a primary biofilm;

a2) allowing an air-saturated blank water sample to pass through the primary biofilm obtained in step a1) to purge the primary biofilm, until a stable DO reduction current is tested and obtained;

a3) allowing an air-saturated standard solution to pass through the primary biofilm purged in said step a2), and testing and obtaining DO reduction current of said standard solution;

a4) repeating the processes of step a1) to step a3), until the tested DO reduction current of the standard solution is stable, so as to complete the microorganism cultivation and obtain a biofilm.

In order to obtain a biofilm with saturated microbial adsorption, in the method of the present invention, firstly under the condition of a thermostatic water bath provided by the above technical solution, i.e. at 20☐-45☐, said air-saturated microorganism-containing water sample continuously flows through the inner surface of a microbial carrier, so as to make microorganisms in said microorganism-containing water sample be adsorbed on the inner surface of said carrier and generate a primary biofilm, and the carrier adsorbed with the primary biofilm is a primary biofilm reactor. In the present invention, the flow rate of said microorganism-containing water sample flowing through the microbial carrier is preferably 0.5 mL/min-10.0 mL/min.

After obtaining the primary biofilm, a large amount of organic matters are adsorbed on said primary biofilm, thus these organic matters adsorbed on the biofilm will consume DO. In order to purge off said organic matters, the present invention allows an air-saturated blank water sample to flow through said primary biofilm to purge said primary biofilm, and purge off the residual organic matters therein. In this process, the endogenous respiration of the biofilm consumes a certain amount of DO in said blank water sample. Said blank water sample flows through said primary biofilm, and then flows to an oxygen electrode, and said oxygen electrode tests the content of residual DO in the effluent blank water sample. Preferably, the present invention allows said air-saturated blank water sample to flow through said biofilm reactor continuously. When the output current of the oxygen electrode is stable, the DO reduction current value of said blank water sample is obtained. In the present invention, said blank water sample is one or more of tap water, well water, rain water or groundwater, and preferably one or two of tap water or groundwater. In prior art, a buffer solution system is commonly adopted to maintain the activity stability of the biofilm. In the method of the present invention, the blank water sample selected from one or more of tap water, well water or groundwater may meet the demands of normal biological activity of microorganisms due to the specific microbial population in the membrane and membrane-forming method. In the present invention, the flow rate of said blank water sample flowing through said primary biofilm is preferably 0.5 mL/min-10.0 mL/min, and more preferably 1.0 mL/min-3.0 mL/min; and the time for performing microbial primary cultivation is preferably 12 hours-150 hours.

After purging said primary biofilm, the present invention allows an air-saturated standard solution to flow through said primary biofilm, and testing is carried out to obtain a stable DO reduction current value of the standard solution. In this process, the endogenous respiration of the primary biofilm consumes a certain amount of DO, while the primary biofilm utilizes organic matters in the standard solution to perform exogenous respiration, and consumes the DO in said standard solution. Said standard solution flows through said primary biofilm, and then flows to the oxygen electrode. Said oxygen electrode tests and outputs the value of oxygen reduction current which indicates the content of residual DO in the effluent standard solution. In order to obtain a stable DO reduction current value, preferably the present invention allows the standard solution to flow through said primary biofilm continuously, until the output current of the oxygen electrode is stable, and the DO reduction current of said standard solution is obtained. In the present invention, when said standard solution passes through said primary biofilm, because the exogenous respiration of microorganisms consumes the DO in the standard solution, the tested stable DO reduction current of the standard solution is lower than the stable DO reduction current when said blank water sample passes through said biofilm reactor, and the difference is related to the BOD concentration of said standard solution. The present invention has no special limitation on said technical solution for testing DO reduction current, and the technical solution for testing current-time curve of the oxygen electrode that is well known to the skilled in the field can be adopted.

In the present invention, said standard solution is preferably a standard solution prescribed by Organization for Economic Co-operation and Development (OECD), a glucose solution, a glutamic acid solution, a mixed solution of glucose and glutamic acid, or a sucrose solution, more preferably a glucose solution or a mixed solution of glucose and glutamic acid, and most preferably a mixed solution of glucose and glutamic acid, i.e. GGA solution. Said OECD solution is a standard solution used in BOD determination process recommended in OECD standard, and said OECD solution contains beef extract, peptone and urea and the like. In the present invention, said standard solutions are all prepared and diluted by adopting one or more in said tap water, well water, rain water or groundwater in the above technical solution. BOD concentration of the standard solution in the present invention refers to the BOD content of the standard solution under a certain volume, and its unit is mg $O_2/L$. The BOD concentration of the standard solution in the present invention is not higher than 100.0 mg $O_2/L$. In order to ensure that the contact time of the blank water sample with the biofilm is consistent with that of the standard solution with the biofilm, the flow rates of said blank water sample and standard solution flowing through said biofilm reactor are kept consistent, preferably 0.5 mL/min-10.0 mL/min, and more preferably 1.0 mL/min-3.0 mL/min.

In order to obtain a biofilm with saturated microbial adsorption, the primary cultivation for the biofilm and the test steps for the air-saturated blank water sample and standard solution, i.e. the processes of said step a1) to step a3) in the above technical solution, are carried out repeatedly according to the above teaching. In the present invention, said biofilm primary cultivation and the test process for said air-saturated blank water sample and standard solution are preferably repeated once every 3-12 hours, and more preferably every 4-5 hours, until the tested DO reduction current difference between the blank water sample and the standard solution is constant, which indicates that microbial adsorption on the inner surface of the reactor is saturated, the cultivation for the biofilm is completed and a stable biofilm is obtained.

After obtaining the stable biofilm, the present invention performs testing for the target water sample according to the process of: firstly testing the content of DO of an air-saturated blank water sample, allowing an air-saturated blank water sample to flow through said stable biofilm, testing the blank water sample flowing through the biofilm reactor by use of an oxygen electrode, when the output current of the oxygen electrode is stable, the obtained DO reduction current of said air-saturated blank water sample is recorded as $i_0$, which represents the DO content of the blank water sample after oxygen is consumed by endogenous respiration of the biofilm;

after obtaining the DO reduction current of the blank water sample, allowing an air-saturated target water sample to flow through the biofilm through which the blank water sample has been passed, testing the target water sample flowing through said biofilm by use of an oxygen electrode, when the output current of the oxygen electrode is stable, the DO reduction current of said air-saturated target water sample is recorded as $i_s$, which represents the DO content of the target solution after oxygen is consumed by endogenous respiration and exogenous respiration of the biofilm. When said target water sample flows through said biofilm, microorganisms in said biofilm perform exogenous respiration, degrade the organic matters in said target water sample, and consume a portion of DO in said target water sample. Therefore, the obtained DO reduction current value of said target water sample is lower than that of said blank water sample;

After obtaining the DO reduction current of said air-saturated blank water sample and the DO reduction current of said air-saturated target water sample according to the above technical solution, the DO reduction current difference between said blank water sample and said target water sample can be determined, i.e. $\Delta\ i = i_0 - i_s$, and said DO reduction current difference is the basis for calculating BOD of said target water sample.

After obtaining the DO reduction current difference of said air-saturated target water sample, the BOD of the target water sample can be determined according to said DO reduction current difference and a predetermined standard solution standard curve. In present invention, said standard solution standard curve is preferably obtained according to the steps of:

preparing air-saturated standard solutions having series BOD concentrations by use of the blank water sample provided in the above technical solution as solvent;

allowing an air-saturated blank water sample to pass through the biofilm obtained in the above technical solution, and testing and determining the DO reduction current of said blank water sample;

allowing said standard solution to pass through the biofilm through which said blank water sample has passed, and testing and determining the DO reduction current of said standard solution;

determining the difference between the DO reduction current of said blank water sample and the DO reduction current of said standard solution according to the DO reduction current of said blank water sample and the DO reduction current of said standard solution;

and determining a standard curve according to said difference and the BOD concentration of said standard solution.

In the present invention, standard solutions having a series of BOD concentrations are firstly prepared by use of the blank water sample provided in the above technical solution, i.e. one or more of tap water, well water, rain water or groundwater, as solvent. The present invention has no special limitation on the source of said standard solution, and the standard solution used in BOD determination that is well known to the skilled in the field can be adopted. In present invention, said standard solution is preferably a standard solution prescribed by Organization for Economic Co-operation and Development (OECD), a glucose solution, a glutamic acid solution, a mixed solution of glucose and glutamic acid, or a sucrose solution, more preferably a glucose solution or a mixed solution of glucose and glutamic acid, and most preferably a mixed solution of glucose and glutamic acid, i.e. GGA solution. Said OECD solution is a standard solution used in BOD determination process recommended in OECD standard, and said OECD solution contains beef extract, peptone and urea and the like. BOD concentration of said standard solution in the present invention refers to the BOD content of said standard solution in a certain volume, and its unit is mg $O_2$/L. In the present invention, the adopted standard solution BOD concentration range depends on various factors such as the flow rate of the water sample and the volume of a carrier for the biofilm. When the BOD concentration of the standard solution exceeds a specific concentration, the amount of oxygen gas consumed by the biofilm no longer increases, so that when the BOD concentration of a target water sample is likely to be higher than said specific concentration, the target water sample should be diluted with said blank water sample and then measured. The selection of the range of the standard solution BOD concentration is well known to one skilled in the art. In present invention, the BOD concentration of the standard solution used for preparing the standard curve is preferably 1.0 mg $O_2$/L-60.0 mg $O_2$/L, and more preferably 2.0 mg $O_2$/L-30.0 mg $O_2$/L.

In the process, the testing scheme for the DO reduction current of said air-saturated blank water sample is the same as that for the DO reduction current of said air-saturated blank water sample in the biofilm preparation process recited in the above technical solution. The DO reduction current of said air-saturated blank water sample is obtained by testing the air-saturated blank water sample via the method provided in the above technical solution. In the process, the testing scheme for the DO reduction current of said air-saturated standard solution is the same as that for said air-saturated target water sample provided in the above technical solution. The DO reduction current of said air-saturated standard solution is obtained by testing said air-saturated standard solution via the method provided in the above technical solution.

After completing the testing for one standard solution with a certain BOD concentration, the present invention performs a testing for another standard solution. That is, the present invention tests the DO reduction current of said air-saturated blank water sample, tests and determines the value of the DO reduction current of the another standard solution with another BOD concentration, and then determines the DO reduction current difference between the blank water sample and standard solution; in this manner, the present invention completes the testing for standard solutions of all BOD concentrations, and obtains the difference of the DO reduction current for the standard solution of each BOD concentration.

In present invention, when said air-saturated standard solution flows through the biofilm, microorganisms in the biofilm perform exogenous respiration, degrade the organic matters in said standard solution, and consume DO therein. Therefore, after said air-saturated standard solution passes through said biofilm, its oxygen reduction current value decreases. The present invention deducts the DO reduction current of said air-saturated standard solution from the DO reduction current of said air-saturated blank water sample, so as to obtain the DO reduction current difference corresponding to said air-saturated standard solution.

In the present invention, a standard curve is plotted according to the obtained DO reduction current difference values corresponding to the respective standard solutions and the respective BOD concentrations. That is, the present invention adopts the BOD concentrations of the standard solutions as X coordinate, and adopts the obtained DO reduction current differences for the corresponding standard solutions as Y coordinate, and then performs analysis of linear equation to obtain the standard curve of the standard solution.

After obtaining the standard curve, the present invention calculates BOD concentration of the target water sample according to the DO reduction current difference, i.e. said $\Delta i$ of the target water sample obtained according to the above technical solution, and the standard curve.

In order to meet the demands of biofilm reactor cultivation and a rapid BOD testing, the present invention preferably adopts the reaction flow shown in FIG. 1 to test the BOD of a target water sample.

Referring to FIG. 1, wherein 1 is a computer, 2 is a first data line, 3 is an electrochemical workstation, 4 is a second data line, 5 is an oxygen electrode, 6 is an oxygen electrode liquid outlet, 7 is an oxygen electrode liquid inlet, 8 is a reactor, 9 is a peristaltic pump, 10 is an electromagnetic valve, 11 is a first injection tube, 12 is a second injection tube, 13 is a third injection tube, 14 is a water sample container, 15 is a tap water container, 16 is a standard solution container, 17 is a sampling pump, 18 is a water source, 19 is a sample outlet tube, and 20 is a thermostatic water bath; said computer 1, said electrochemical workstation 3 and said oxygen electrode 5 are sequentially connected via said first data line 2 and said second data line 4, respectively; the oxygen electrode 5, reactor 8, and peristaltic pump 9 are sequentially connected with the sample outlet tube 19; said first injection tube 11, said second injection tube 12, said injection tube 13 and said sample outlet tube 19 communicate with said electromagnetic valve; said first injection tube 1, said second injection tube 12 and said third injection tube 13 communicate with said actual water sample container 14, tap water container 15 and standard solution container 16, respectively; and the water source 18 communicates with the sampling pump 17.

The present invention adopts the flow shown in FIG. 1 to test the BOD of a target water sample, and the specific process is as follows:

The present invention firstly performs the cultivation of a biofilm in the reactor 8 to obtain a biofilm reactor. More specifically, the present invention firstly starts said thermostatic water bath 20, said thermostatic water bath is used for, on one hand, ensuring a consistent temperature of the water sample in the water sample container 14, the tap water in the tap water container 15 and the standard solution in the standard solution container 16, and under the condition of air saturation, the three have consistent DO content; on the other hand, ensuring that the formation of the biofilm on the inner surface of the reactor is completed under a thermostatic condition; under the thermostatic condition, the present invention samples from the water source 18 via the sampling pump 17 to the water sample container 14 in advance, wherein the water source 18 is a microorganism-containing water sample, and microorganism-containing water sample in the water sample container 14 is subjected to air saturation to obtain air-saturated microorganism-containing water sample; the air-saturated microorganism-containing water sample in the water sample container 14 is fed to the reactor 8 through the first injection tube 11, the electromagnetic valve 10, the sample outlet tube 19 and the peristaltic pump 9 in sequence; while the sampling pump 17 supplements the microorganism-containing water sample from the water source 18 towards the water sample container 14 at a rate consistent with that of the peristaltic pump 9. When the microorganism-containing water sample flows through the reactor 8, microorganisms therein are gradually adsorbed on the inner wall of the reactor 8 and grow by use of the organic matters in the water sample, so that the microorganism cultivation is started; said air saturation rate is 3.0 L/min, the water sample flow rate controlled by the peristaltic pump 9 is 2.0 mL/min, the thermostatic water bath 20 is set at 37☐, and the cultivation time of the primary biofilm reactor is about 36 h.

After obtaining the primary biofilm reactor, tap water from the tap water container 15 is adopted to clean said primary biofilm reactor, the GGA solution in the standard solution container 16 is tested to evaluate the growth condition of the primary biofilm, so as to obtain finally the biofilm reactor with saturated microbial adsorption. The present invention firstly makes the air-saturated tap water in the tap water container 15 flow through the reactor 8 with adsorbed microorganisms through the second injection tube 12, electromagnetic valve 10, sample outlet tube 19 and peristaltic pump 9 in sequence to clean the residual organic matters in the system, until the DO reduction current signal outputted by the oxygen electrode 5 tested by the electrochemical workstation 3 is stable. At this time, the stable DO reduction current value represents the residual DO content in tap water discharged after the air-saturated tap water is subjected to oxygen consumption via endogenous respiration of the biofilm; after completing the cleaning for the system, the present invention adopts the above microorganism-adsorbed reactor 8 to test the GGA solution. More specifically, the present invention places the pre-prepared GGA solution in the standard solution container 16, performs air saturation on the GGA solution in said standard solution container 16 to obtain air-saturated GGA solution; makes said air-saturated GGA solution flow through the microorganism-adsorbed reactor 8 through the third injection tube 13, electromagnetic valve 10, sample outlet tube 19 and peristaltic pump 9 in sequence. The DO in said air-saturated GGA solution is consumed by microorganism population adsorbed in the primary biofilm reactor, so that the DO reduction current signal of said GGA solution outputted by said oxygen electrode 5 is lower than that of the above air-saturated tap water, and the decreased value of the current signal, i.e. DO reduction current difference, represents the amount of DO consumed by the microorganisms adsorbed in the reactor 8;

In order to determine whether the microbial adsorption in the reactor 8 is saturated, the present invention repeats said microbial primary cultivation, tap water cleaning (purging) and GGA testing, until the decreased value of the DO reduction current signal obtained by testing said GGA solution is consistent with first two testing results, which indicates that the amount of microorganisms adsorbed in the reactor 8 reaches the constant state. At this time the microorganism cultivation is completed, and a stable biofilm reactor is obtained for testing BOD;

After obtaining the biofilm reactor, the present invention replaces the first injection tube 11 and the sample outlet tube 19 in the testing system with another injection tube and another sample outlet tube, so as to test the GGA solutions of a series of BOD concentrations and test the target water sample, plots a standard curve according to the testing results for the GGA solutions was well as the BOD concentrations, and calculate BOD of the target water sample according to said standard curve and the testing results for said target water sample;

In order to obtain the standard curve, the present invention firstly prepares GGA solutions of a series of BOD concentrations, and places said GGA solutions in said standard solution container 16, respectively, performs air saturation for the GGA solutions in said standard solution container 16 to obtain air-saturated GGA solutions; the present invention performs the testing on the GGA solutions of a series of BOD concentrations for said air-saturated GGA solution according to said testing process for the GGA solution provided in the above technical solution, to obtain the DO reduction current differences corresponding to the GGA solutions of each BOD concentrations, and plots the standard curve according to said DO reduction current differences and BOD concentrations of the GGA solutions t;

After obtaining the standard curve, the present invention tests a target water sample. Before the testing for the target water sample, the present invention cleans said system with tap water according to said process in the above technical solution, so as to obtain the DO reduction current value of air-saturated tap water. After completing the cleaning for the system, the present invention introduces target water sample of the water source 18 into the water sample container 14 through the sampling pump 17, and performs air saturation for the target water sample in the water sample container 14 to obtain air-saturated target water sample. Said air-saturated target water sample flows through the biofilm reactor 8 through the first injection tube 11, electromagnetic valve 10, sample outlet tube 19 and peristaltic pump 9 in sequence, and DO therein is consumed by the microorganisms adsorbed in the biofilm reactor, so that the DO reduction current value of the target water sample outputted by the oxygen electrode 5 and obtained by the electrochemical workstation 3 is lower than that of the air-saturated tap water and DO reduction current difference thus is obtained. According to the obtained DO reduction current difference and standard curve, the BOD of the target water sample is obtained.

The present invention adopts activated sludge, surface water, domestic sewage or microorganism-containing industrial wastewater as microorganism-containing water samples, microorganisms are cultivated through the adsorption and growth process on the inner surface of the carrier to obtain a biofilm, which is applied in the testing for BOD. The microorganisms in the obtained biofilm in the present invention are from nature, have very strong adaptive capacity to environment, and can survive and propagate in complex water quality conditions. In prior art, in order to ensure the biological activity of microorganisms, a buffer system is a necessary element for testing BOD, which can adjust the pH value of the system, and provide the osmotic pressure for maintaining microbial activity. In present invention, one or more of tap water, well water, rain water or groundwater is adopted to substitute the buffer system in prior art, and used for cleaning the biofilm, preparing and diluting the standard solution, and diluting the target water sample, and one or more of said tap water, well water, rain water or groundwater can meet the normal biological activity of the biofilm. On one hand, said cultivation method of the biofilm in the present invention retains natures of microorganisms in the microorganism-containing water sample as much as possible, so that activity thereof is not obviously influenced by the change of system pH value and ion concentration, and the biofilm can resist a suitable change of external conditions; on the other hand, said tap water, well water, rain water or groundwater water contain various kinds of trace elements, a certain amount of metal ions and trace amount of organic matters, these conditions are enough to meet demands of normal physiological activity of the microorganisms. Therefore, the testing method of the present invention has no need of adopting a buffer system, which reduces the testing cost, for example, avoiding the consumption of a buffer reagent, and the preparation of pure water and a buffer solution, and also avoids secondary pollution caused by buffer solution such as phosphates.

In addition, the adoption of one or more of tap water, well water, rain water or groundwater as blank water sample will not cause significant errors on the measurement result, because the organic matter content in tap water, well water, rain water or groundwater is very low. The weak oxygen consumption due to the organic matter is regarded as endogenous respiration and has been deducted in the testing process for blank water sample, so that the obtained testing result has higher accuracy.

After obtaining the biofilm, the present invention selects GGA solution, adds poisonous substances with a series of mass concentrations, and tests the anti-poisoning performance and stability of the biofilm. More specifically, the testing process for anti-poisoning performance is as follows:

Adding the poisoning substances with a series of mass concentrations into the GGA solutions with a certain BOD concentration, so as to obtain GGA solutions containing poisonous substance;

testing and determining the DO reduction current differences of said GGA solutions containing poisoning substance, according to said method for testing the target water sample in the above technical solution;

and testing and determining the anti-poisoning performance of said biofilm, according to the DO reduction current differences of said GGA solutions containing poisoning substance and the predetermined DO reduction current difference of GGA solution without poisoning substance.

The present invention preferably tests the influence of heavy metal ions and organic poisoning substances among the poisonous substances on said biofilm. Said heavy metal ion preferably is $Cr^{6+}$, $Cu^{2+}$, $Zn^{2+}$, $Ni^{2+}$ or $Mn^{2+}$ that is common in wastewater, and said organic poisoning substance preferably is 3,5-dichlorophenol that is common in wastewater. The present invention tests the influence of the poisonous substances of a series of BOD concentrations on said biomembrane (biofilm).

The GGA solutions containing heavy metal ion $Cr^{6+}$, $Cu^{2+}$, $Zn^{2+}$, $Ni^{2+}$ or $Mn^{2+}$ with mass concentration of 1.0 mg/L-30.0 mg/L are tested by said method in the above technical solution. Experimental results show that: the obtained DO reduction current difference is basically consistent with that of the GGA solution without heavy metal ion, which indicates that these heavy metal ions have no obvious inhibitory action on the biofilm constructed in present invention, and indicates that said biofilm has better resistance to heavy metal ion poisoning; further the present invention performs testing for the GGA solutions containing 3,5-dichlorophenol with mass concentration of 1.0 mg/L-30.0 mg/L, experimental results show that: the DO reduction current difference increases with the increase of 3,5-dichlorophenol mass concentration, and shows a good linear relation, which indicates that 3,5-dichlorophenol can be degraded by microorganism population in the biofilm. Therefore, in the method for testing BOD provided in the present invention, organic poisoning substance 3,5-dichlorophenol exhibits the properties of an organic substance, rather than the properties of an poisoning substance. It can be seen that the prepared biofilm in the present invention has better anti-poisoning performance when it is applied in the testing for BOD.

The testing for the stability of said biofilm in the present invention is carried out as follows:

in a testing day, performing repeated testing for the GGA solution with known BOD concentration according to said method in the above technical solution, so as to obtain the DO reduction current differences of said GGA solution;

obtaining BOD of said GGA solution according to mean value of the DO reduction current differences of said GGA solution and said standard curve in the above technical solution;

and comparing the BOD of said GGA solution obtained in testing day and the known BOD concentration of said GGA solution, and obtaining the stability of the prepared biomembrane reactor in the present invention based on the compared results. In non-testing days, the biofilm reactor is filled with tap water, and stored at room temperature.

The present invention takes a GGA solution with BOD concentration of 16.0 mg $O_2$/L as an example to test the stability of said biofilm. In the present invention, from Monday to Friday, repeatedly testing is preformed on said GGA solution for seven times every day, continuously for 8 weeks, so that the DO reduction current difference mean value of said GGA solution for each day is obtained, BOD of said GGA solution is obtained according to said DO reduction current difference mean value and said standard curve in the above technical solution. The stability test result of said biofilm is determined by comparing the tested BOD of said GGA solution with the BOD of GGA solution obtained according to the international standard method. The experimental results of continuous 8 weeks show that the value of BOD of said GGA solution is maintained about 16.0 mg $O_2$/L, which indicates that the prepared biofilm in the present invention has higher stability.

The present invention provides a method for testing BOD, the method provided in the present invention adopts activated sludge, surface water, domestic sewage or microorganism-containing industrial wastewater as a microorganism-containing water sample, performs air saturation, and then makes it continuously flow through a microbial carrier, and finally obtains a biofilm on the inner wall of the carrier; makes an air-saturated blank water sample and a target water sample flow through said biofilm in sequence, and test and determine the DO reduction current of said blank water sample and said target water sample. Microorganisms in the biofilm degrade the organic matters in the target water sample, and consume the DO therein, so that the DO reduction current value of said target water sample is lower than that of said blank water sample, and the DO reduction current differences corresponding to said target water sample is obtained. The BOD of said target water sample is determined according to said DO reduction current difference and a predetermined standard curve. Said blank water sample is one or more of tap water, well water, rain water or groundwater. The method for testing BOD provided in the present invention adopts activated sludge, surface water, domestic sewage or microorganism-containing industrial wastewater as the microorganism-containing water sample. Said microorganism-containing water sample is from natural world, and is subjected to microorganism cultivation to obtain a biofilm. Said biofilm retains the inherent relatively high adaptive capacity to environment of microorganisms in the microorganism-containing water sample, so that there is no need of providing environment of a buffer solution therefor. In one or more of tap water, well water, rain water or groundwater, said biofilm is able to have normal biological activity, so that it can degrade the pollutants in a target water sample. BOD of the target water sample is obtained according to the amount of the consumed DO. The method provided in the present invention has no need of adopting a buffer solution, which avoids the pollution on environment caused by the buffer solution such as phosphates, and reduces the testing cost.

In order to further illustrate the present invention, the method for testing BOD provided in the present invention will hereinafter be described in detail in conjunction with embodiments, but they can not be understood as limiting the scope of the present invention.

EXAMPLE 1

According to the schematic diagram shown in FIG. 1, a biofilm reactor was prepared. One end of the biofilm reactor was connected with an oxygen electrode 5, the oxygen electrode 5 was accessed in an electrochemical workstation 3 with CHI832b type, and said electrochemical workstation 3 monitored the current change of the oxygen electrode 5, and the current change was displayed by a computer 1.

The thermostatic water bath 20 was activated, and the temperature was adjusted to 30□. Activated sludge water sample 300 mL was injected into the water sample container 14 from the water source 18 via the sampling pump 17, and said activated sludge water sample was subjected to air saturation at a rate of 3.0 L/min. The glass reactor 8 with a length of 105.0 cm and an inside diameter of 2.0 mm was placed in the thermostatic water bath. The activated sludge water sample was transported to the reactor 8 through the first injection tube 11, the electromagnetic valve 10 and the sample outlet tube 19 at a rate of 1.0 mL/min, and then reached the surface of the oxygen electrode 5 after flowing through the reactor 8. At the same time, activated sludge water sample was continuously supplemented to the water sample container 11 from the water source 18. After 24 hours, tap water 300 mL was injected into the tap water container 15, and subjected to air saturation at a rate of 3.0 L/min. Under the control of the peristaltic pump 9, tap water reached the reactor 8 through the second injection tube 12, the electromagnetic valve 10, and the sample outlet tube 19 at a rate of 1.0 mL/min, and then reached the surface of the oxygen electrode 5, and the DO reduction current was recorded as 533 nA. GGA solution with BOD concentration of 20.0 mg $O_2$/L was injected into the standard solution container 16, and subjected to air saturation at a rate of 3.0 L/min. Under the control of the peristaltic pump 9, the obtained air-saturated GGA solution reached the biofilm reactor 8 through the third injection tube 13, the electromagnetic valve 10 and the sample outlet tube 19 at a rate of 1.0 mL/min, and then reached the surface of the oxygen electrode 5 after flowing through the biomembrane reactor 8. The electrochemical workstation 3 monitored the change of current of the oxygen electrode 5. When the oxygen electrode current was stable, the DO reduction current was recorded as 449 nA. The difference of the DO reduction current when tap water flowed through the surface of the oxygen electrode 5 and when GGA solution flowed through the surface of the oxygen electrode 5 was obtained by calculation, i.e. 533 nA−449 nA=84 nA. The difference represented the signal response of the GGA solution with BOD concentration of 20.0 mg $O_2$/L on the obtained primary biofilm reactor. The cultivation step for the above biofilm reactor was carried out repeatedly. After 12 h, the above tap water cleaning and the testing step for the GGA solution with BOD concentration of 20.0 mg $O_2$/L were carried out repeatedly, and new DO reduction current difference was recorded as 121 nA. The above steps were carried out repeatedly, and when the cultivation was carried out for 68 h, the output current of the oxygen electrode 5 was 344 nA as the GGA solution with BOD concentration of 20.0 mg $O_2$/L was tested. At this time, the stable DO reduction current difference when tap water flowed through the oxygen electrode surface and when the GGA solution flowed through the oxygen electrode surface was 195 nA. The result was basically consistent with the DO reduction current difference obtained when cultivation was carried out for 60 h, which indicated that the inner wall of the reactor 8 had been adsorbed with saturated microorganisms, which means the cultivation for the biofilm reactor had been completed, at the time, and a stable biofilm reactor was obtained.

EXAMPLE 2

The thermostatic water bath 20 was activated, and the temperature was adjusted to 30□. Tap water of 300 mL was injected into the tap water container 15, and subjected to air saturation at a rate of 3.0 L/min. Under the control of the peristaltic pump 9, the air-saturated tap water reached the biofilm reactor through the second injection tube 12, the electromagnetic valve 10 and the sample outlet tube 19 at a rate of 1.0 mL/min, and then flowed through said biofilm reactor to reach the surface of the oxygen electrode 5. The electrochemical workstation 3 monitored the change of the oxygen electrode current. When the oxygen electrode current was stable, the DO reduction current was recorded as 539 nA.

Glucose 150 mg and glutamic acid 150 mg were dissolved in tap water, and diluted to a constant volume of 100 mL to obtain mother liquor of the GGA solution with BOD concentration of 1980.0 mg $O_2$/L. A portion of said mother liquor was diluted with tap water, so as to obtain GGA solutions with BOD concentrations of 1.0 mg $O_2$/L, 5.0 mg $O_2$/L, 10.0 mg $O_2$/L, 15.0 mg $O_2$/L, 20.0 mg $O_2$/L, 25.0 mg $O_2$/L, 30.0 mg $O_2$/L and 40.0 mg $O_2$/L, respectively. In the present invention, firstly the GGA solution with BOD concentration of 1.0 mg $O_2$/L was injected into the standard solution container 16, and subjected to air saturation at a rate of 3.0 L/min. Under the control of the peristaltic pump 9, the obtained air-saturated GGA solution reached the biofilm reactor prepared in example 1 through the third injection tube 13, the electromagnetic valve 10 and the sample outlet tube 19 at a rate of 1.0 mL/min, and then reached the surface of the oxygen electrode 5 through said biofilm reactor. The electrochemical workstation 3 monitored the change of oxygen electrode current. When the oxygen electrode current was stable, the DO reduction current was recorded as 522 nA, and the stable DO reduction current difference between when tap water flowed through the oxygen electrode surface and when the GGA solution flowed through the oxygen electrode surface was recorded, i.e. 539 nA−522 nA=17 nA. The difference indicated the signal response of the GGA solution with BOD concentration of 1.0 mg $O_2$/L on the biofilm reactor. The above tap water cleaning (purging) step was repeated, and the DO reduction current value when the oxygen electrode was stable was recorded. Then the GGA solutions with other BOD concentrations were tested in sequence according to the above steps. When the GGA solution with BOD concentration of 40.0 mg $O_2$/L was tested, it was found that the decrease of its signal response compared with the GGA solution with BOD concentration of 30.0 mg $O_2$/L was not obvious. The reason for this phenomenon is probably that: as the BOD concentration of the GGA solution increases, the DO therein is insufficient to be utilized by the biofilm, which results in the decrease of degradation efficiency of the GGA solution. Therefore, the GGA solution at the concentration is not applicable for the preparation of the standard curve under the experimental conditions.

Figure 2:
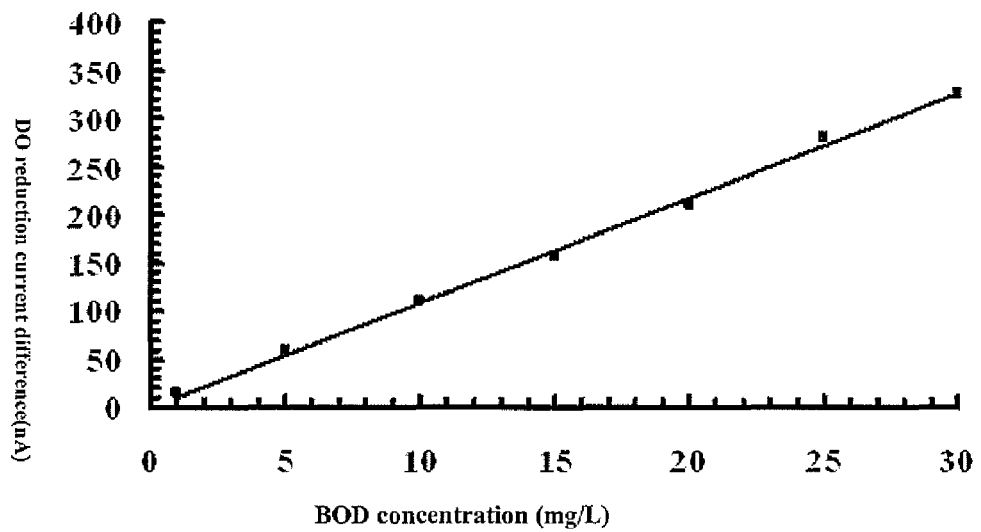
FIG. 2 is a standard curve obtained in example 2 of the present invention.

After obtaining the DO reduction current differences of the GGA solutions of said BOD concentrations, the present invention plotted the standard curve of the GGA solution with the BOD concentration values 1.0 mg $O_2$/L-30.0 mg $O_2$/L of the GGA solutions as X coordinate (horizontal axis), and the corresponding differences of signal response on the oxygen electrode after passing through the biofilm reactor as Y coordinate (vertical axis), and the result was shown in FIG. 2. FIG. 2 was the standard curve obtained in example 2 in the present invention, FIG. 2 showed that there is a good linear relation between the DO reduction current difference and the corresponding BOD concentration for the GGA solution. After linear fitting, a standard curve equation $\Delta i$ (nA)=10.87 C (mg O2/L) was obtained, wherein $\Delta i$ was the DO reduction current difference and its unit was nA, C was BOD concentration, its unit was mg $O_2$/L, and its linear range was 1.0 mg $O_2$/L-30.0 mg $O_2$/L.

EXAMPLE 3

The thermostatic water bath 20 was activated, and the temperature was adjusted to 30□. Tap water 300 mL was injected into the tap water container 15, and subjected to air saturation at a rate of 3.0 L/min. Under the control of the peristaltic pump 9, the obtained air-saturated tap water reached the reactor 8 through the second injection tube 12, the electromagnetic valve 10 and the sample outlet tube 19 at a rate of 1.0 mL/min, and then reached the surface of the oxygen electrode 5 after flowing through the reactor 8. The electrochemical workstation 3 monitored the change of the oxygen electrode current. When the oxygen electrode current was stable, the DO reduction current was recorded as 538 nA.

Water sample obtained from a secondary precipitation pool of the second sewage treatment plant in Changchun city of China was subjected to air saturation at a rate of 3.0 L/min. Under the control of the peristaltic pump 9, the water sample in the water sample container 14 reached the reactor 8 through the first injection tube 11, the electromagnetic valve 10 and the sample outlet tube 19 at a rate of 1.0 mL/min, and then reached the surface of the oxygen electrode 5 after flowing through the reactor 8. The electrochemical workstation 3 monitored the change of oxygen electrode current. When the oxygen electrode current was stable, the DO reduction current was recorded as 489 nA. Its signal response i.e. the difference between the DO reduction current of the blank solution and the DO reduction current of the to-be-treaded water sample, was calculated and determined as 49 nA.

The BOD value of the water sample in the secondary precipitation pool of the sewage treatment plant was calculated and determined as 4.5 mg $O_2$/L according to the signal response obtained in the present example and the standard curve obtained in example 2 under the same experimental conditions.

EXAMPLE 4

According to the schematic diagram shown in FIG. 1, a biofilm reactor was prepared. One end of the biofilm reactor was connected with an oxygen electrode 5, the oxygen electrode 5 was accessed in an electrochemical workstation 3 with CHI832b type, and said electrochemical workstation 3 monitored the current change of the oxygen electrode 5, and the current change was displayed by a computer 1.

The thermostatic water bath 20 was activated, and the temperature was adjusted to 37° C. Water sample 300 mL obtained from the South Lake was injected into the water sample container 14 from the water source 18 via the sampling pump 17, and South Lake water sample was subjected to air saturation at a rate of 3.0 L/min. The ethylene-vinyl acetate copolymer reactor 8 with a length of 220.0 cm and an inside diameter of 1.6 mm was placed in the thermostatic water bath 20. Under the control of the peristaltic pump 9, South Lake water sample reached the reactor 8 through the first injection tube 11, the electromagnetic valve 10 and the sample outlet tube 19 at a rate of 2.0 mL/min, and then reached the surface of the oxygen electrode 5 after flowing through the reactor 8. At the same time, South Lake water sample was continuously supplemented to the water sample container 14 from the water source 18. After 48 h, tap water 300 mL was injected into the tap water container 15, and subjected to air saturation at a rate of 3.0 L/min. Under the control of the peristaltic pump 9, the air-saturated tap water reached the reactor 8 through the second injection tube 12, the electromagnetic valve 10, the sample outlet tube 19 at a rate of 2.0 mL/min, and then reached the surface of the oxygen electrode 5 after flowing through the reactor 8. The electrochemical workstation 3 monitored the change of oxygen electrode current, and when the oxygen electrode current was stable, the DO reduction current was recorded as 446 nA.

A GGA solution with BOD concentration of 4.0 mg $O_2$/L was injected into the standard solution container 16, and subjected to air saturation at a rate of 3.0 L/min. Under the control of the peristaltic pump 9, the air-saturated GGA solution reached the reactor 8 through the third injection tube 13, the electromagnetic valve 10 and the sample outlet tube 19 at a rate of 2.0 mL/min, and then reached the surface of the oxygen electrode 5 after flowing through the reactor 8. The electrochemical workstation 3 monitored the change of oxygen electrode current, and when the oxygen electrode current was stable, the DO reduction current was recorded as 401 nA. Finally the stable DO reduction current difference between when tap water flowed through the oxygen electrode surface and when the GGA solution flowed through the oxygen electrode surface was calculated and obtained, i.e. 446 nA−401 nA=45 nA. The difference represents the signal response of the GGA solution with BOD concentration of 4.0 mg $O_2$/L on the primary biofilm reactor. The above cultivation step for the above biofilm reactor was repeated. After 12 h, the above tap water cleaning and the testing step for GGA solution with BOD concentration of 4.0 mg $O_2$/L were repeated, and therefore the new signal response was recorded as 52 nA. Then the above steps were continuously repeated, wherein after the cultivation was carried out to 86 h, when the GGA solution with BOD concentration of 4.0 mg $O_2$/L was tested, the output current of the oxygen electrode was 366 nA. At the time, the stable DO reduction current difference between when tap water flowed through the oxygen electrode surface and when the GGA solution flowed through the oxygen electrode surface was 80 nA. The result was basically consistent with the DO reduction current difference obtained when the cultivation was carried out to 78 h, which indicated that the inner wall of the reactor 8 had been adsorbed with saturated microorganisms and the cultivation for the biofilm reactor was completed. Therefore a stable biofilm reactor was obtained.

EXAMPLE 5

According to the schematic diagram shown in FIG. 1, a biofilm reactor was prepared. One end of the biofilm reactor was connected with an oxygen electrode 5, the oxygen electrode 5 was accessed in an electrochemical workstation 3 with CHI832b type, and said electrochemical workstation 3 monitored the current change of the oxygen electrode 5, and the current change was displayed by a computer 1.

The thermostatic water bath 20 was activated, and the temperature was adjusted to 37° C. Water sample of milk plant 300 mL was injected into the water sample container 14 from the water source 18 via the sampling pump 17, and then was subjected to air saturation at a rate of 3.0 L/min. A silicone reactor 8 with a length of 75.0 cm and an inside diameter of 1.6 mm was placed in the thermostatic water bath 20. Under the control of the peristaltic pump 9, the air-saturated water sample of milk plant reached the reactor 8 through the first injection tube 11, the electromagnetic valve 10 and the sample outlet tube 19 at a rate of 0.5 mL/min, and then reached the surface of the oxygen electrode 5 after flowing through the reactor 8. At the same time, the water sample of milk plant was continuously supplemented to the water sample container 14 from the water source 18. After 48 h, tap water 300 mL was injected into the tap water container 15, and subjected to air saturation at a rate of 3.0 L/min. Under the control of the peristaltic pump 9, the air-saturated tap water reached the reactor 8 through the second injection tube 12, the electromagnetic valve 10 and the sample outlet tube 19 at a rate of 0.5 mL/min, and then reached the surface of the oxygen electrode 5 after flowing through the reactor 8. The electrochemical workstation 3 monitored the change of oxygen electrode current, and when the oxygen electrode current was stable, the DO reduction current was recorded as 625 nA.

GGA solution with BOD concentration of 10.0 mg $O_2$/L was injected into the standard solution container 16, and subjected to air saturation at a rate of 3.0 L/min. Under the control of the peristaltic pump 9, the air-saturated GGA solution reached the reactor 8 through the third injection tube 13, the electromagnetic valve 10 and the sample outlet tube 19 at a rate of 0.5 mL/min, and then reached the surface of the oxygen electrode 5 after flowing through the reactor 8. The electrochemical workstation 3 monitored the change of oxygen electrode current, and when the oxygen electrode current was stable, the DO reduction current was recorded as 507 nA, the stable DO reduction current difference between when tap water flowed through the oxygen electrode surface and when the GGA solution flowed through the oxygen electrode surface was calculated and obtained, i.e. 625 nA−507 nA=118 nA. The difference represented the signal response of the GGA solution with BOD concentration of 10.0 mg $O_2$/L on the primary biofilm reactor. The cultivation step for the above biofilm reactor was repeated. After 12 h, the above tap water cleaning and the testing step for the GGA solution with BOD concentration of 10.0 mg $O_2$/L were repeated, and new signal response was recorded as 148 nA. Then the above steps were continuously repeated, wherein after the culture was carried out for 76 h, when the GGA solution with BOD concentration of 10.0 mg $O_2$/L was tested, the output current of the oxygen electrode was 455 nA. At this time, the stable DO reduction current difference between when tap water flowed through the oxygen electrode surface and when the GGA solution flowed through the oxygen electrode surface was 180 nA. The result was basically consistent with the DO reduction current difference obtained when the culture was carried out to 70 h, which indicated that the inner wall of the reactor 8 had been adsorbed with saturated microorganisms, and the culture for the biofilm reactor was completed. Thus a stable biofilm reactor was obtained.

EXAMPLE 6

The thermostatic water bath 20 was activated, and the temperature was adjusted to 30° C. Tap water 300 mL was injected in the tap water container 15, and subjected to air saturation at a rate of 3.0 L/min. Under the control of the peristaltic pump 9, the air-saturated tap water reached the reactor 8 through the second injection tube 12, the electromagnetic valve 10 and the sample outlet tube 19 at a rate of 1.0 mL/min, and then reached the surface of the oxygen electrode 5 after flowing through the reactor 8. The electrochemical workstation 3 monitored the change of the oxygen electrode current, and when the oxygen electrode current was stable, the DO reduction current was recorded as 405 nA.

GGA solutions with BOD concentrations of 0.25 mg $O_2$/L, 0.50 mg $O_2$/L, 0.75 mg $O_2$/L and 1.0 mg $O_2$/L were prepared according to said method in example 2. Tap water was injected into the standard solution container 16, and subjected to air saturation at a rate of 3.0 L/min. Under the control of the peristaltic pump 9, the air-saturated tap water reached the reactor 8 through the third injection tube 13, the electromagnetic valve 10 and the sample outlet tube 19 at a rate of 1.0 mL/min, and then reached the surface of the oxygen electrode 5 after flowing through the reactor 8. The electrochemical workstation 3 monitored the change of oxygen electrode current, and when the oxygen electrode current was stable, the DO reduction current was recorded as 404 nA. At the case, the signal response was 1 nA, which was regarded as the normal fluctuation in oxygen electrode itself error range. The GGA solutions with BOD concentrations of 0.25 mg $O_2$/L, 0.50 mg $O_2$/L, 0.75 mg $O_2$/L and 1.0 mg $O_2$/L were tested in sequence according to said method in example 2 to obtain testing curves and corresponding signal responses.

Figure 3:
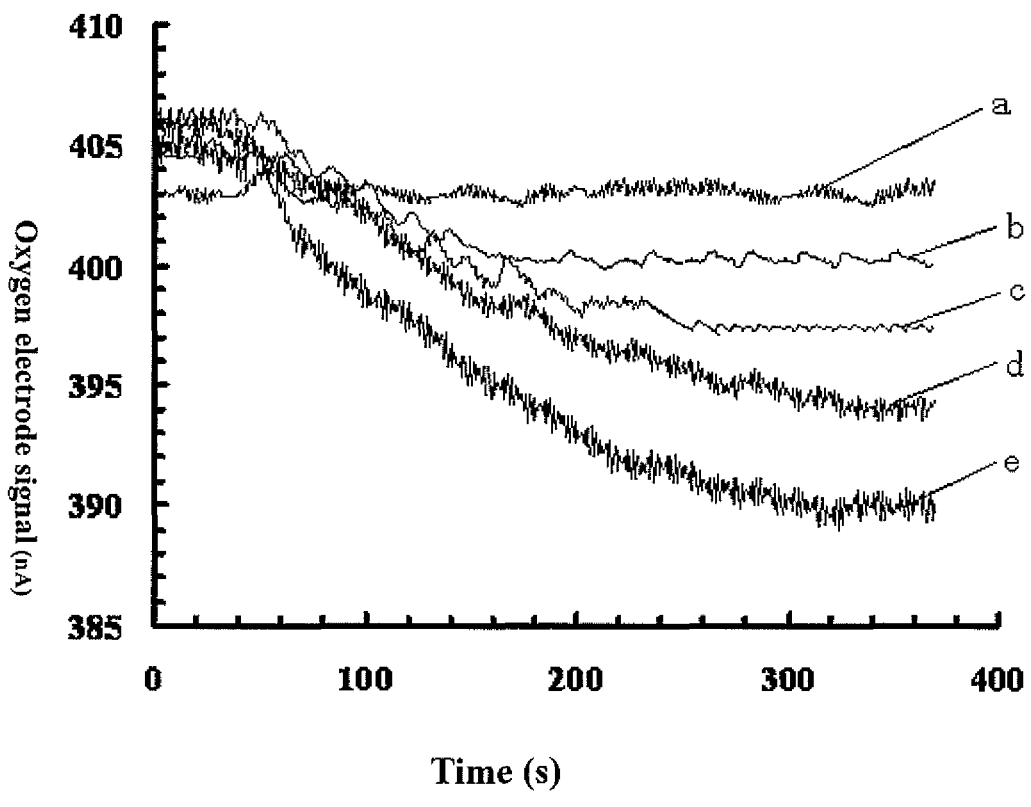
FIG. 3 is a testing result obtained in example 6 of the present invention.

The results were shown in FIG. 3. FIG. 3 was the experimental results of testing limit obtained in the example 6 in the present invention, wherein curve 1, curve 2, curve 3, curve 4 and curve 5 were the DO reduction current response curves of the GGA solutions with BOD concentration of 0 mg $O_2$/L, 0.25 mg $O_2$/L, 0.50 mg $O_2$/L, 0.75 mg $O_2$/L and 1.0 mg $O_2$/L, respectively. It can be seen from the FIG that when tap water was tested, the oxygen electrode output current did not substantively change, but when the GGA solution with BOD of 0.25 mg $O_2$/L was tested, the oxygen electrode output current signal obviously decreased. With the increase of the GGA concentration, the decreased degree of the oxygen electrode output current signal increased. Therefore, it was determined that the testing lower limit of the method provided in the present invention for the water body was about 0.25 mg $O_2/L$.

EXAMPLE 7

The thermostatic water bath 20 was activated, and the temperature was adjusted to 30□. Tap water 300 mL was injected into the tap water container 15, and subjected to air saturation at a rate of 3.0 L/min. Under the control of the peristaltic pump 9, the air-saturated tap water reached the reactor 8 through the second injection tube 12, the electromagnetic valve 10 and the sample outlet tube 19 at a rate of 1.0 mL/min, and then reached the surface of the oxygen electrode 5 after flowing through the reactor 8. The electrochemical workstation 3 monitored the change of oxygen electrode current, and when the oxygen electrode current was stable, the DO reduction current was recorded as 544 nA.

GGA solutions containing heavy metal ion $Cr^{6+}$, $Cu^{2+}$, $Zn^{2+}$, $Ni^{2+}$ and $Mn^{2+}$ of a series of mass concentrations, 0.0 mg/L, 1.0 mg/L, 3.0 mg/L, 6.0 mg/L, 8.0 mg/L, 10.0 mg/L, 15.0 mg/L, 20.0 mg/L and 30.0 mg/L, respectively and containing poisonous substance 3,5-dichlorophenol with BOD concentration of 16.0 mg $O_2/L$ were prepared. According to said step for testing the GGA solution in example 2, the GGA solutions containing heavy metal ion or 3,5-dichlorophenol obtained in the example were tested, and their signal responses were recorded.

Figure 4:
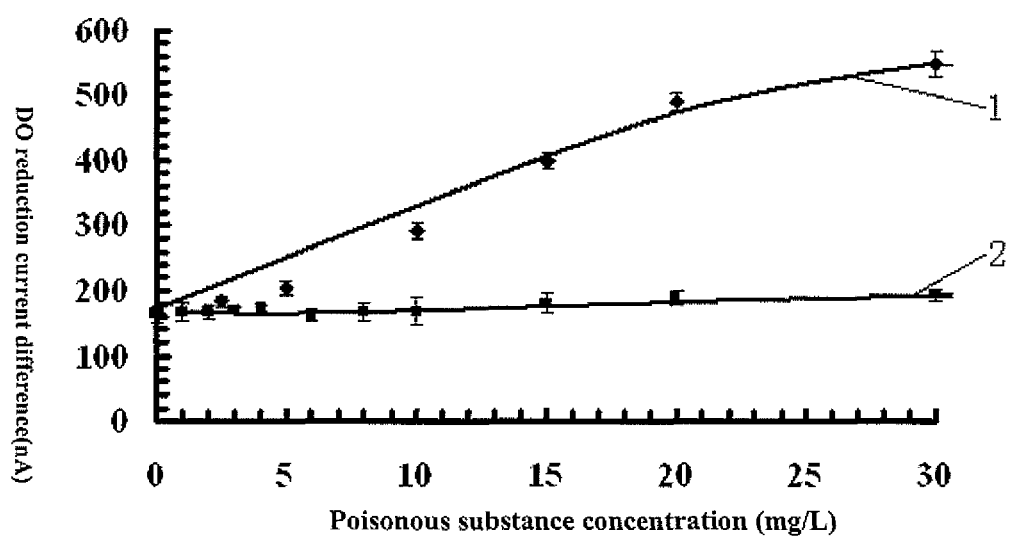
FIG. 4 is a test result of resistance to $Cr^{6+}$ and 3,5-dichlorophenol poisoning of a biofilm reactor obtained in example 7 of the present invention.
Figure 5:
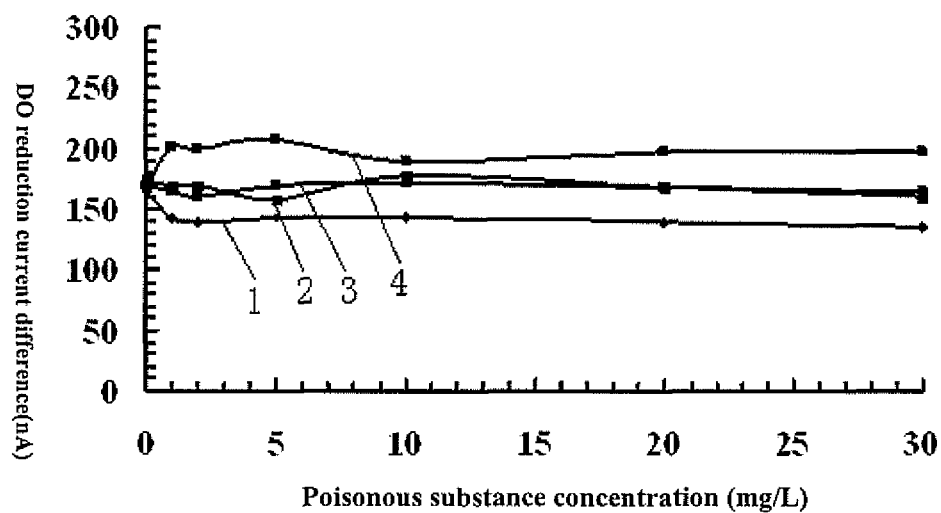
FIG. 5 is a test result of resistance to $Cu^{2+}$, $Zn^{2+}$, $Ni^{2+}$ and $Mn^{2+}$ poisoning of a biofilm reactor obtained in example 7 of the present invention.

After obtaining the signal responses of the GGA solutions containing poisonous substances, the present invention obtained the influence test result of the poisonous substances on the biofilm reactor with the mass concentration of poisonous substance as X-coordinate and its corresponding signal response as Y-coordinate, and the results were shown in FIG. 4 and FIG. 5. FIG. 4 was the experimental results of the resistance to $Cr^{6+}$ and 3,5-dichlorophenol of the biofilm reactor obtained in example 7 in the present invention. In the FIG. 4, the curve 1 was the test result of 3,5-dichlorophenol resistance, and the curve 2 was the test result of $Cr^{6+}$ resistance; FIG. 5 was the experimental results of resistance to $Cu^{2+}$, $Zn^{2+}$, $Ni^{2+}$ and $Mn^{2+}$ of the biofilm reactor obtained in example 7 in the present invention. In FIG. 5, the curve 1 was the test result of $Zn^{2+}$ resistance, the curve 2 was the test result of $Ni^{2+}$ resistance, the curve 3 was the test result of $Mn^{2+}$ resistance, and the curve 4 was the test result of $Cu^{2+}$ resistance; It can be seen from FIG. 4 and FIG. 5, in the case of the presence of heavy metal ions, the tested and obtained current difference of the GGA solution was basically consistent with the current difference of the GGA solution without heavy metal ions, which indicated that these heavy metal ions had no obvious inhibitory action on the biofilm reactor prepared in the present invention; and in the case of the presence of 3,5-dichlorophenol, its current difference increased with the increase of 3,5-dichlorophenol concentration, which indicated that 3,5-dichlorophenol can be degraded by the biofilm reactor. That is, in the method provided in the present invention, 3,5-dichlorophenol exhibited the properties of an organic substance, rather than the properties of a poisonous substance. Therefore, the biofilm reactor provided in the present invention had good anti-poisoning performance.

EXAMPLE 8

According to said method for testing GGA solution in example 2, the GGA solution with BOD concentration of 16.0 mg $O_2/L$ was repeatedly tested for 7 times every day from Monday to Friday, to test the stability of the biofilm reactor provided by the present invention.

Figure 6:
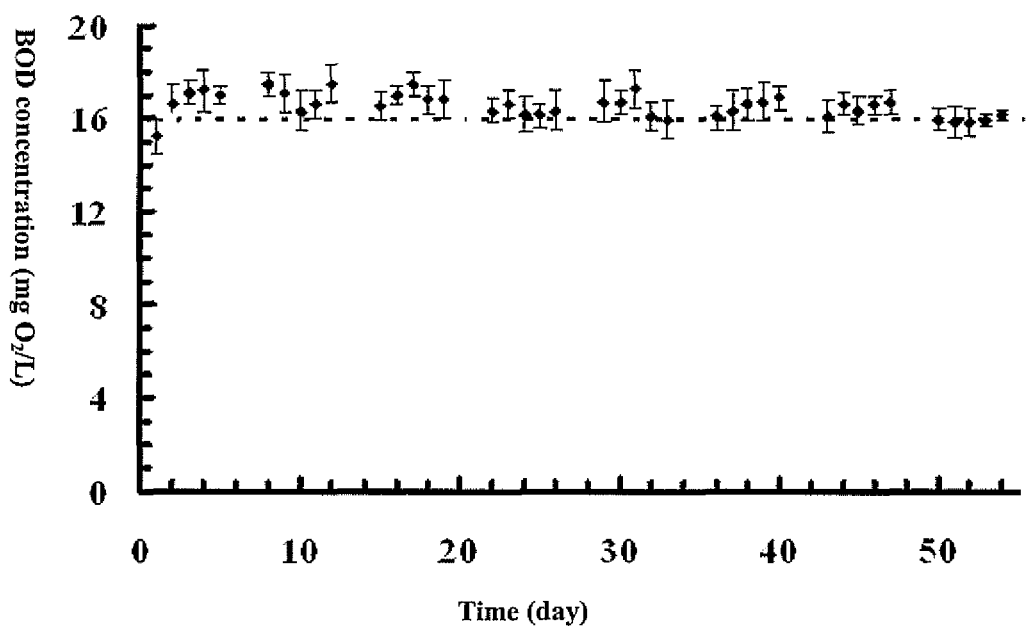
FIG. 6 is a test result of stability of a biofilm reactor obtained in example 8 of the present invention.

The results were shown in FIG. 6. FIG. 6 was the stability test result of the biofilm reactor obtained in example 8 in the present invention. It can be seen from FIG. 6 that the testing results for the GGA solution with BOD concentration of 16.0 mg $O_2/L$ were all at about 16.0 mg $O_2/L$, which indicated that the biofilm reactor provided by the present invention had higher stability and the testing result was accurate.

Through the above examples, it can be seen that: there is provided a testing method for BOD in the present invention in which activated sludge, surface water, domestic sewage, or industrial wastewater without poisonous effect on microorganisms is used as a microorganism-containing water sample to perform microorganism cultivation for said microorganism-containing water sample, so as to obtain a biofilm; the present invention allows a target water sample to pass through the above obtained biofilm, tests and determines the decrease of DO reduction current value of the target water sample; the decreased value of the DO reduction current value has good linear relation with its BOD, and then according to a predetermined standard curve to obtain the BOD of the target water sample can be calculated. The method provided in the present invention can complete the determination of BOD of water sample in the environment condition provided by one or more of tap water, well water, rain water or groundwater, because the microorganism population cultivated by means of the adopted microorganism-containing water sample via said culture method in the above technical solution have stronger environmental adaptability, and their activity is not obviously influenced by the change of pH value and ion concentration. Furthermore, tap water, well water, rain water or groundwater contains various kinds of microelements, a certain amount of metal ions and trace amount of organic matters, which conditions are sufficient to meet the demands of normal physiological activity of microorganisms in the microorganism-containing water source. Therefore, the biofilm cultivated and obtained in the present invention can survive in a non-buffer system, so as to avoid the adoption of a buffer system, avoid the secondary pollution on environment caused by phosphate buffer solution in buffer solutions, and reduce the testing cost.

The above description is only to make one skilled in the art better understand the present invention, and it should be noted that, for those skilled in the art, without departing from the principles of the invention, also a number of improvements and modifications can be made, these improvements and modifications should also be considered as the scope of the invention.

What is claimed is:
1. A method for detecting biochemical oxygen demand (BOD), comprising the steps of:
   a) subjecting an air-saturated microorganism-containing water sample to microorganism cultivation to obtain a biofilm;
   b) allowing an air-saturated blank water sample to pass through the biofilm obtained in said step a), and determining a dissolved oxygen (DO) reduction current of said blank water sample;
   c) allowing an air-saturated target water sample to pass through the biofilm having been subjected to said step b), and determining a DO reduction current of said target water sample;
   d) calculating the difference between the DO reduction current of said blank water sample and the DO reduc- tion current of said target water sample according to the DO reduction current of the blank water sample obtained in said step b) and the DO reduction current of the target water sample obtained in said step c); and e) determining BOD of the target water sample according to the difference obtained in said step d) and a predetermined standard curve;

wherein said microorganism-containing water sample is activated sludge, surface water, domestic sewage or microorganism-containing industrial wastewater; and said blank water sample is one or more selected from tap water, well water, rain water and groundwater.

2. The detection method according to claim 1, characterized in that said microorganism-containing water sample is activated sludge, surface water or microorganism-containing industrial wastewater.

3. The detection method according to claim 1, characterized in that said step a) comprises:

a1) at 20° C.-45° C., subjecting an air-saturated microorganism-containing water sample to microbial primary cultivation to obtain a primary biofilm;

a2) allowing an air-saturated blank water sample to pass through the primary biofilm obtained in said step a1) to purge said primary biofilm, until an stable DO reduction current is obtained;

a3) allowing an air-saturated standard solution to pass through the primary biofilm purged in said step a2), and determining a DO reduction current of said standard solution; and a4) repeating the step a1) to step a3), until the determined DO reduction current of the standard solution is stable, so as to complete the microorganism cultivation and obtain a biofilm.

4. The detection method according to claim 1, characterized in that said blank water sample is tap water and/or groundwater.

5. The detection method according to claim 1, characterized in that in said step a), the microorganism cultivation is performed for 20-300 hours.

6. The detection method according to claim 1, characterized in that the standard curve in said step e) is obtained by:

preparing air-saturated standard solutions having a series of BOD concentrations by using said blank water sample as solvent;

allowing an air-saturated blank water sample to pass through the biofilm obtained in said step a), and determining a stable DO reduction current of said blank water sample;

allowing said standard solutions to pass through the biofilm through which said blank water sample has passed, and determining DO reduction currents of said standard solutions;

determining the differences between the DO reduction current of said blank water sample and the DO reduction currents of said standard solutions according to the DO reduction current of said blank water sample and the DO reduction currents of said standard solutions; and determining a standard curve according to said differences and the BOD concentrations of said standard solutions.

7. The detection method according to claim 3, characterized in that said standard solutions are glucose solutions, glutamic acid solutions, mixed glucose-glutamic acid solutions or sucrose solutions.

8. The detection method according to claim 3, characterized in that the BOD concentrations of said standard solutions are in the range of 1.0 mg $O_2$/L-60.0 mg $O_2$/L.

9. The detection method according to claim 1, characterized in that the microorganism cultivation in said step a) is performed in a reactor.

10. The detection method according to claim 9, characterized in that said reactor is tubular;

the material of said reactor is glass, ethylene-vinyl acetate copolymer, plastic, nylon, quartz or silicone;

said reactor has a length of 30.0 cm-420.0 cm; and said reactor has an inside diameter of 1.0 mm-4.0 mm.

11. The detection method according to claim 6, characterized in that said standard solutions are glucose solutions, glutamic acid solutions, mixed glucose-glutamic acid solutions or sucrose solutions.

12. The detection method according to claim 6, characterized in that the BOD concentrations of said standard solutions are 1.0 mg $O_2$/L-60.0 mg $O_2$/L.

* * * * *